(12) United States Patent
Yeomans

(10) Patent No.: US 11,946,947 B2
(45) Date of Patent: Apr. 2, 2024

(54) METHOD OF VALIDATING A TEST AND APPARATUS FOR USE IN THE METHOD

(71) Applicant: Allan James Yeomans, Gold Coast (AU)

(72) Inventor: Allan James Yeomans, Gold Coast (AU)

( * ) Notice: Subject to any disclaimer, the term of this patent is extended or adjusted under 35 U.S.C. 154(b) by 602 days.

(21) Appl. No.: 17/271,926

(22) PCT Filed: Aug. 13, 2019

(86) PCT No.: PCT/AU2019/050845
§ 371 (c)(1),
(2) Date: Feb. 26, 2021

(87) PCT Pub. No.: WO2020/041822
PCT Pub. Date: Mar. 5, 2020

(65) Prior Publication Data
US 2021/0318218 A1 Oct. 14, 2021

(30) Foreign Application Priority Data

Aug. 30, 2018 (AU) .............................. 2018903203
Oct. 9, 2018 (AU) .............................. 2018903804

(51) Int. Cl.
*G01N 5/04* (2006.01)
*G01N 31/12* (2006.01)
*G01N 33/24* (2006.01)

(52) U.S. Cl.
CPC .............. *G01N 5/04* (2013.01); *G01N 31/12* (2013.01); *G01N 33/24* (2013.01)

(58) Field of Classification Search
CPC .......... G01N 5/04; G01N 31/12; G01N 33/24; G01N 31/005; G01N 31/16; G01N 25/22;
(Continued)

(56) References Cited

U.S. PATENT DOCUMENTS

2015/0247787 A1* 9/2015 Yeomans ............... G01N 5/045
73/865
2019/0033241 A1* 1/2019 Aoki .................... G01N 27/043

FOREIGN PATENT DOCUMENTS

CN 106124357 A * 11/2016 ............... G01N 1/04
JP 2003-240625 A 8/2003
(Continued)

OTHER PUBLICATIONS

English Bibliography of PCT Patent Application Publication No. WO2017163601A1, published Sep. 28, 2017, Printed from Derwent Innovation on Oct. 26, 2022, 6 pages.
(Continued)

*Primary Examiner* — Brandi N Hopkins
(74) *Attorney, Agent, or Firm* — Lippes Mathias LLP

(57) ABSTRACT

A method of validating a test for estimating the organic carbon content of soil or changes in organic carbon content of soil over time in which a first sample of soil is taken from a selected location and heated using Loss On Ignition (LOI) to remove organic carbon, the method comprising the steps of taking a further sample of soil from an adjacent location, the sample having minimal organic material content. A predetermined quantity of an organic material is added to the further sample to provide a second sample which is heated using Loss On Ignition (LOI) with the change of weight of the second sample determining whether the test of the first sample yielded a valid estimate of the organic carbon content of the first sample. Apparatus (10) for use in performing the method is also disclosed.

20 Claims, 8 Drawing Sheets

(58) Field of Classification Search
CPC ........... G01N 33/1846; G01N 21/3504; G01N 1/4022; G01N 1/34; G01N 21/79; G01N 1/44; G01N 30/02; B09B 3/00; G06Q 10/30; F23G 7/14; F26B 25/006; C12M 21/02; C10B 53/02; E21B 36/008; B09C 1/06

See application file for complete search history.

(56) References Cited

FOREIGN PATENT DOCUMENTS

| | | |
|---|---|---|
| WO | 2014/053028 A1 | 4/2014 |
| WO | 2017/163601 A1 | 9/2017 |
| WO | 2017/219097 A1 | 12/2017 |

OTHER PUBLICATIONS

Ball, Loss-on-Ignition as an Estimate of Organic Matter and Organic Carbon in Non-Calcareous Soils, Journal of Soil Science vol. 15, No. 1, Mar. 1964, pp. 84-92.
EP Pat. App. No. 19853972.8, Extended European Search Report, dated Jul. 28, 2022, 12 pages.
International Search Report and Written Opinion dated Oct. 15, 2019.

\* cited by examiner

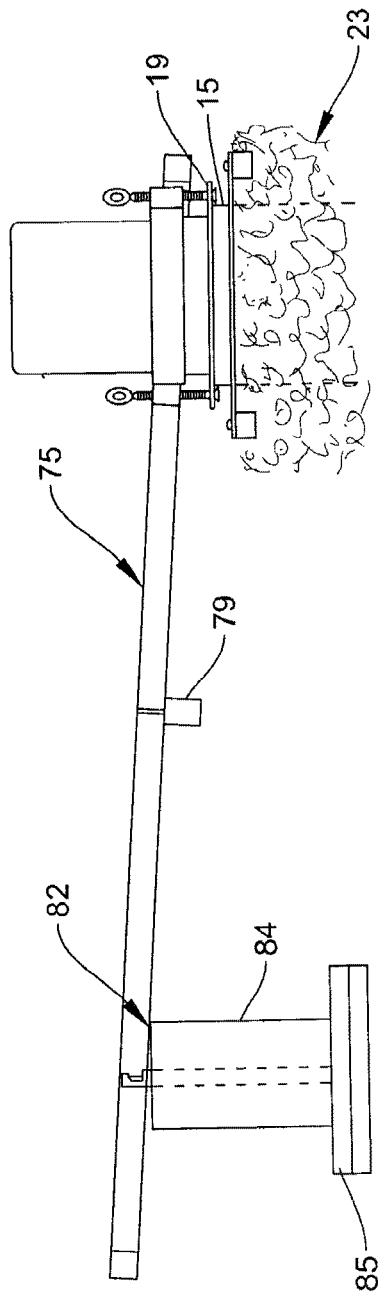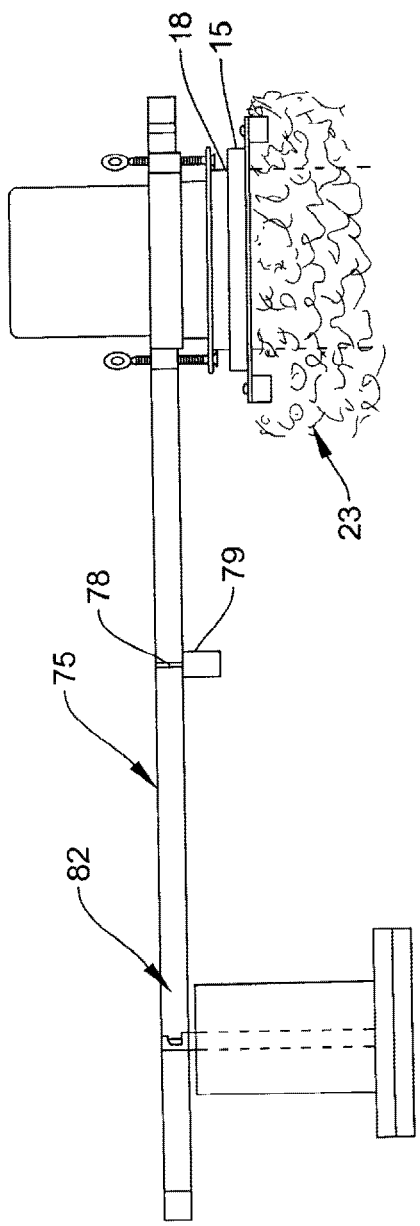

METHOD OF VALIDATING A TEST AND APPARATUS FOR USE IN THE METHOD

TECHNICAL FIELD

This invention relates to a method of validating a test and in particular to a method of validating a test used for assessing or estimating the carbon content of soils. This invention also relates to apparatus for use in method of validation. This invention further relates a method and means for cooling the aforementioned apparatus and more for accurately assessing the carbon content of soils

BACKGROUND ART

It is known to test soils to assess the carbon content of soils by the use of a Loss on Ignition test (LOI). In such a test, a sample of soil is strongly heated which causes volatile substances in the sample to escape until the mass of the sample ceases to change. The difference in weight before and after the ignition test represents the amount of organic material that was present in the sample. The organic carbon content in the soil can then be estimated from this weight change, the organic carbon content being in a known percentage range of organic material in the sample.

In my International patent application No, PCT/AU2013/001511, the contents of which are incorporated by reference herein, I disclose a method of and apparatus for obtaining an estimation of the organic carbon content of soil and/or variations or changes in organic carbon content of soil over time which uses a Loss on Ignition technique In that method, one or more samples of soil are supported on gas permeable barriers arranged placed within an elongated hollow chamber after which a heated gas is supplied to the housing for passage through the soil sample/s to initially remove moisture form the samples to dry the soil samples and thereafter to remove burn off organic materials including organic carbon in the soil sample or samples, with the change of weight of the soil sample/s due to the heating process correlating to the organic carbon content in the soil sample. to be obtained. After a selected period of time subsequent further samples of soil can be taken from the same area and tested as above so that increases in organic carbon content which is equivalent to increases in carbon dioxide sequestration in the soil can serve as a basis for remuneration in a program which rewards carbon dioxide sequestration.

In the method and apparatus disclosed in the aforesaid International patent application a small quantity of soil particles can be forced through the gas permeable means before organic carbon is burnt off which results in small inaccuracies in calculation of the change of weight of the soil samples and thus in the calculation of changes in soil carbon content. It would desirable to have a method and apparatus in which these inaccuracies can be at least substantially eliminated.

Further in both the conventional Loss on Ignition method as well as the method disclosed in my aforesaid International patent application, inaccuracies can arise with certain types of soil. For example, if a soil has high iron content, the heating process may cause a reaction in the soil so that the measured change of weight in the soil before and after the heating process does not provide a true indication of the organic carbon content in the soil. In iron rich soils, for example, the change of weight in the soil sample may be indicate that the soil has less organic carbon content that it actually has.

In addition, burning off of the organic carbon in the soil samples involves high temperatures, typically in the region of 375° C. and above. These temperatures cause the apparatus to heat considerably and as the oven is insulated to as to reach the high temperatures required, it takes considerable time for the oven and *other parts of the apparatus to cool. This then delays a second and subsequent use of the apparatus because an extended period of time is required before the apparatus can again safely be used. It would be desirable to have a method and means for cooling the apparatus as quickly as possible for efficiency of operation, safety and other purposes.

SUMMARY OF THE INVENTION

The present invention thus provides in a first preferred aspect, a method of validating a test for estimating the organic carbon content of soil or changes in organic carbon content of said soil over time in which a first sample of said soil is taken from a selected location and heated using Loss On Ignition (LOI) to remove organic materials including organic carbon from said soil sample by burning off or oxidising said organic materials, said method comprising the steps of taking at least one further sample of soil from a location immediately adjacent to, and having the same geological structure as said selected location, said sample having or being treated to have minimal organic material content, adding to said further sample, a predetermined quantity of an organic material to provide a second sample, heating said second sample containing said quantity of organic material using Loss On Ignition (LOI) to burn off said quantity of organic material, and monitoring the change of weight of said second sample due to the burning off of said organic materials.

The change of weight in the second sample should be equal to the weight of the organic material added to the soil sample in which case the test is validated and no correction to the results is necessary. Should the weights not match, a reaction between the added organic material and inert material is indicated which means a correction is required to be made to the result.

The organic material added to the soil sample may be any organic material however a preferred organic material for use in the method comprises peat. The initial soil sample after initial heating is inert so that any subsequent measured change of weight of the second sample including the added organic material is due solely to the added organic material The method referred to above uses a loss on ignition (LOI) principle in which a sample of material is strongly heated which causes volatile substances in the sample to escape until the mass of the sample ceases to change. In the present invention, heating of the first soil sample and subsequent heating of the second sample is achieved by passing heated air or gas through the samples for a sufficient time and at selected temperatures until the weight of the samples ceases to change, the loss of weight being due to organic material including organic carbon being burnt off and oxidised. Preferably, the gas flow through the samples is controlled to control the temperature of the samples to ensure that the temperature thereof does not exceed a predetermined temperature or range of temperatures. Controlling the gas flow through the samples of soil controls oxygen flow through the samples and therefore controls the burning of materials in the samples and ensures that the temperature of the samples does not exceed the predetermined temperature or range of temperatures.

The validation method may be used In any Loss on Ignition testing process however it is preferred that the method be undertaken with apparatus of the type disclosed in my International Patent Application No, PCT/AU2013/001151. That apparatus comprises an housing defining an upright elongated chamber, gas permeable means for supporting one or more samples of said soil within said chamber, means for forcing heated gas downwardly through said chamber and the soil sample or samples therein to initially remove moisture from the soil sample or samples to dry said sample or samples and subsequently remove by burning off or oxidising organic materials including carbon from the soil sample or samples and means for measuring the change of weight of said soil sample or samples due to said removal of said organic materials to provide an indication of organic carbon content of the soil or changes in the organic carbon content of the soil. When applied to the validation of the test, organic material of known weight is added to the soil sample or samples after the above heating and organic material removal process and the procedure repeated.

Preferably, a plurality of soil samples are used and the soil samples are arranged within the chamber in series such that heated gas can be passed through the respective soil samples in turn. Preferably the housing and thus chamber have a central longitudinal axis with an inlet at one end for heated gas and an outlet at the other end. Preferably respective soil samples are arranged longitudinally along the axis of the chamber. Preferably the housing is of a tubular configuration and thus the chamber is of a circular cross section.

Preferably respective gas permeable means are provided to support the one or more soil samples within the chamber. Suitably the gas permeable means form barriers which extend diametrically of the chamber. The gas permeable means may comprise a soil sample holder which includes a grid or grating.

Means are suitably provided for weighing the housing containing the soil sample/s before and after the organic materials/carbon removal process to enable calculation of the change of weight in the soil sample/s whilst they remain in situ within the housing to provide an indication of organic carbon content in the soil sample/s. The weighing means is also used in the validation method for weighing the soil sample and added organic material before and after the subsequent reheating process to enable the change of weight thereof to be determined. The change of weight should be equal to the weight of the organic material added to confirm the test as a valid test as the weight of the soil sample after the first heating process, being inert, should not change.

The weighing means may comprise a beam balance having a beam or lever which has a central fulcrum, means on one side of the fulcrum for supporting the housing and means on the opposite side of the fulcrum for carrying a variable counter or balance weight. The housing may be suspended from the beam on one side of the fulcrum such as by means of a knife edge suspension. Preferably, the housing includes one or more hanger members to enable the housing to be suspended via the knife-edge suspension from the beam. Preferably the housing remains connected to the beam during the heating and oxidation process such that at the end of that process, the balance beam can be used for determining the total change in weight of the housing including the soil samples without the need to remove the soil samples from the housing.

Most preferably, the samples are obtained using an auger, the auger being operated to a first depth at a particular location to extract materials to provide a first sample. Preferably, continued operation of the auger to depths below the first depth provide materials for the samples to be used for validation of the results as described further below.

Alternatively the samples can be obtained by using an auger for example of the type disclosed in my International Patent Application PCT/AU2017/050648. Such an auger may be operated to a first depth at a particular location to extract materials to provide a first sample. Subsequently, by continuing operating the auger downwards, after first removing all the above materials to provide the first sample, into the subsoil where negligible soil organic matter can be expected to provide a second sample.

If the test using the base which has been subject the LOI shows a greater LOI loss than predicted then a chemical reaction must have happened between (probably) the carbon in the organic matter and the already "cooked", and therefore, supposedly, inert sample material. Thus an adjustment of the results of the test on the first sample will need to be made to obtain the correct organic carbon content of the sample. If the LOI testing of the base which has not been subject to a LOI test before the peat has been added is then subject to a LOI test, that test will show a LOI weight loss which can be considered to be the same as would result from a test of on a nearby soil which has a weight of organic matter content exactly the same as the weight of peat added to the subsoil material. For more accurate results, a series of Loss on Ignition (LOI) tests can be carried out using the subsoil material which contains no organic matter or little organic matter to which is added a different but known quantity of organic matter. By taking a series of tests a graph can then be drawn which plots the tested by Loss on Ignition (LOI) weights against the known weight of organic matter added to each sample. This graph can be used to show that when any future sample, taken from the same general location is subjected to a Loss On Ignition test the Loss on Ignition weight thus determined can be applied to the graph and the true organic matter content of the soil can be seen and carbon content determined.

Preferably soil particles forced through or past said gas permeable means are collected, and the change of weight of the soil samples adjusted for the weight of said collected soil particles provides an indication of the organic carbon content in the soil sample.

The present invention in a further aspect provides apparatus for obtaining an indication of the carbon content of soil and/or variations of the carbon content in soil in accordance with the above described method, the apparatus comprising an upright housing defining a chamber, a soil sample holder for supporting one or more samples of said soil within the chamber, mean for forcing heated gas through said chamber and the soil sample or samples therein to remove organic carbon from the soil, means for collecting soil particles forced through of past the soil sample holder and means for measuring the change of weight of said soil sample or samples adjusted for the weight of said collected soil particles to provide an indication of carbon content in the soil.

Preferably, the housing is received coaxially within an outer tubular housing such that the walls of the respective housings are juxtaposed, the outer tubular housing being arranged within an outer casing and being surrounded by an insulating material.

The particle collection device is preferably located within a chamber vertically beneath the housings and the outer housing or an extended portion thereof extends into the chamber.

The particle collection device preferably is in the form of a tray which is slidably movable within the chamber. The chamber suitably is defined by a horizontally extending duct and the lower portion of the outer housing extends into the duct. Preferably, the horizontally extending duct is joined at one end to a vertically extending duct which acts as a stack or chimney for discharge of hot air or gases from the apparatus.

Preferably the opposite end of the horizontally extending duct is open and the collection device includes a face member so as to be in the configuration of a drawer wherein when the collection device is slid in a first direction the facing member can overly and close the duct opening and wherein when the collection device is slid in an opposite direction, said face member moves away from and opens the opening, Preferably when the opening is open, air forced into the apparatus cools the apparatus and when flowing through the stack, induces a back pressure which will induce a further flow or air into the apparatus through the opened duct.

Preferably means are provided for creating a forced flow or air through the exhaust duct. Such means suitably comprises a fan, blower or other forced air source and means for connecting the fan, blower or forced air source to the interior of the exhaust duct. Preferably the connecting means comprises a pipe which extends from the blower or fan into the duct. The pipe suitably is in the form of an elbow having a first leg connected of the fan or blower and a second leg which extends longitudinally of the duct so as to direct air from the fan or blower towards the outlet of the duct.

The housing suitably is weighed before and after the organic carbon removal process. The change of weight should be equal to the weight of the organic material added to confirm the test as a valid test as the weight of the soil sample after the first heating process, being inert, should not change and cannot change when additional organic matter is added prior any heating.

Preferably, an annular space is defined between the housings through which cooling air may pass for cooling of the apparatus. Suitably the inner housing includes an annular flange which normally seats on the upper edge of the outer housing and for cooling purposes, the inner housing may be raised to move the flange away from the upper edge of the outer housing to define an opening there-between to thereby open the annular space to the external atmosphere such that the back pressure will cause cooling air to flow into the annular space through the opening defined by the flange and upper edge of the outer housing. Means for supplying a cooling liquid such as a spray from a nozzle may be provided adjacent the opening such that cooling water may also be introduced into annular space for cooling.

BRIEF DESCRIPTION OF THE DRAWINGS

In order that the invention may be more readily understood and be clear enough and complete enough for it to be performed by a persons skilled in the art, reference will now be made to the accompanying drawings which illustrate a preferred embodiment of the invention and wherein:—

FIGS. 7 and 8 are views along line C-C of FIG. 6 illustrating the operation of the weighing apparatus of FIG. 6;

DETAILED DESCRIPTION OF THE PREFERRED EMBODIMENT

Figure 1:
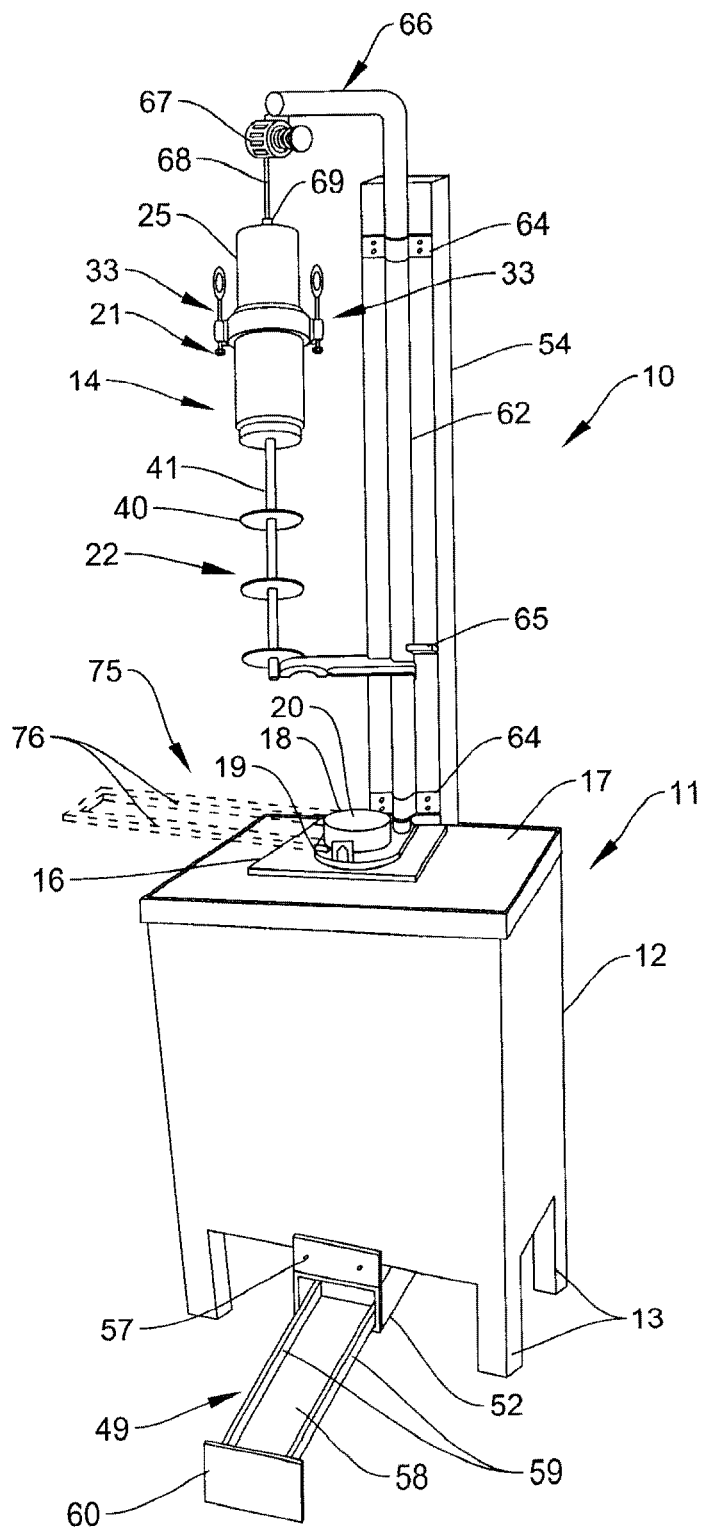
FIG. 1 is an isometric view from the front of apparatus for burning off organic carbon in soil samples according to an embodiment of the invention with the soil sample holder and heater elevated out of the heating chamber.
Figure 2:
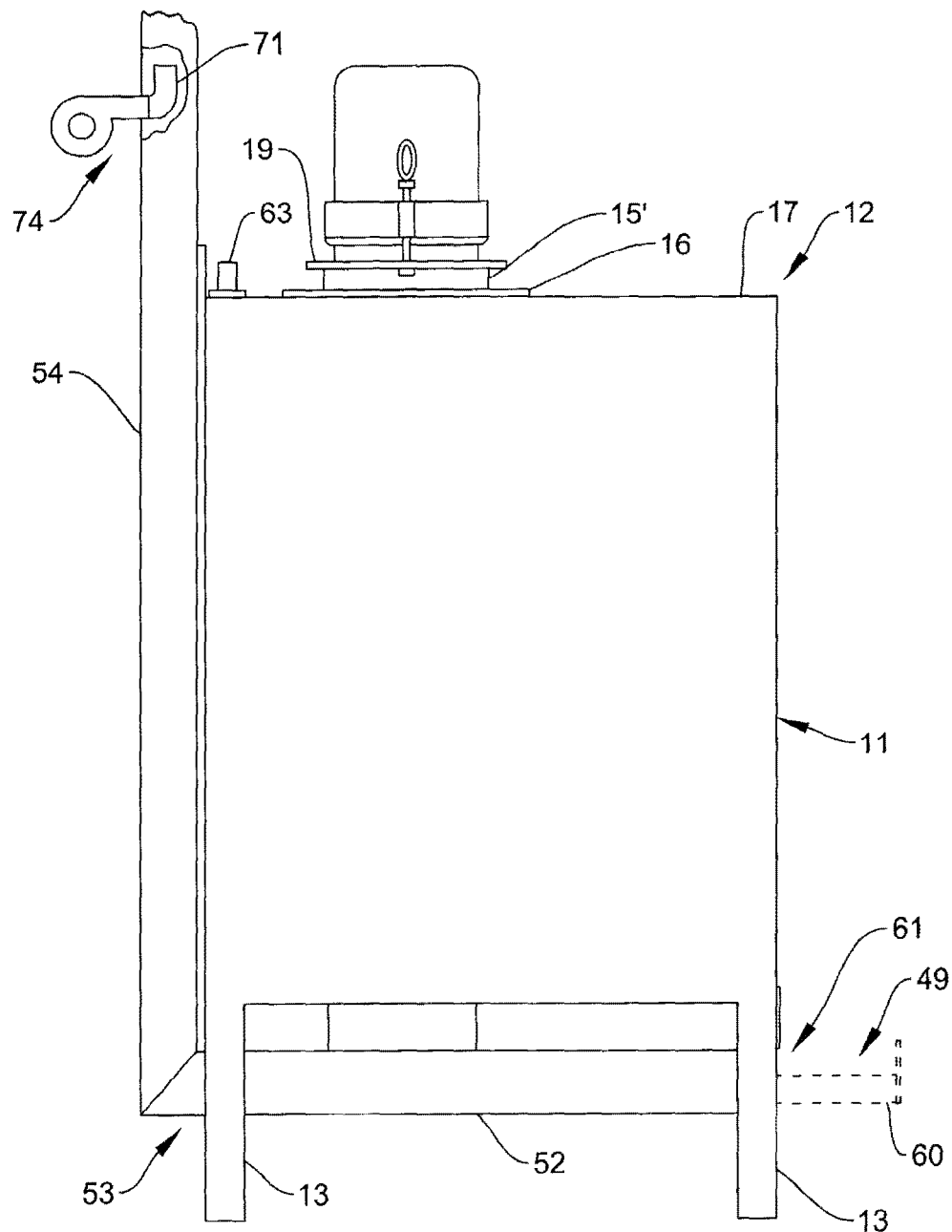
FIG. 2 is a partial side view of the apparatus of FIG. 1 with the soil sample holder and heater lowered for use.

Referring to the drawings and firstly to FIGS. 1 and 2, there is illustrated apparatus 10 for use in heating a sample or samples of soil to remove organic carbon therefrom for the purpose obtaining an indication of the carbon content of the soil sample and for validating results obtained. The apparatus 10 comprises an oven 11 having an outer hollow casing 12 which typically is provided with legs 13 at its lower end whereby the casing 12 may be supported on an underlying surface. Adapted to be supported substantially within the casing 12 is a heating chamber 14 (see also FIG. 3) for use in heating a sample or samples of soil for the purpose of burning off of organic carbon in the soil samples for subsequent assessment of the carbon content of the soil sample and thus the soil from which the sample was taken. The heating chamber 14 is of substantially the same or similar configuration as the heating chamber described in my aforesaid International Patent Application/001151, the contents of which are incorporated by reference herein.

Figure 3:
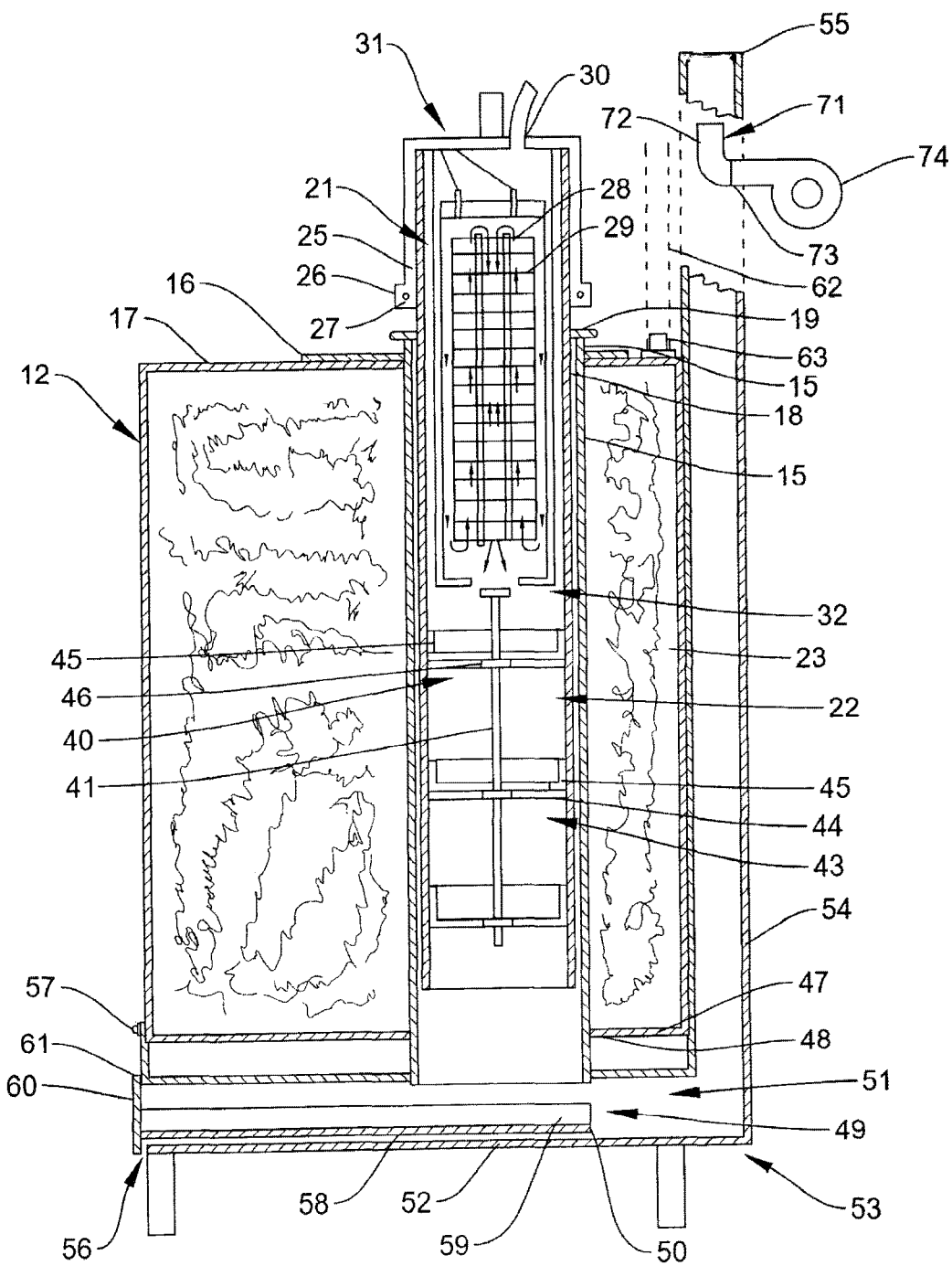
FIG. 3 is a cross-sectional view of the apparatus of FIG. 1 in a plane along line A-A but with the soil sample holder and heater lowered for use.

The heating chamber 14 comprises a main fixed outer elongated tubular housing 15 which is of a circular cross section and which has an flange 16 adjacent its upper end for seating on an upper surface or wall 17 of the casing 12 as shown in FIGS. 1 to 3 so that the housing 15 is supported in an upright attitude The housing 15 extends a small distance above the flange 16 as at 15' and is open at its upper end to receive coaxially therein with clearance an inner tubular housing 18. The housing 18 has an annular flange 19 adjacent it upper end which may seat on the upper end of the extended portion 15' of the housing 15. The upper end of the housing 18 is open at 20 to accept therein a primary air or gas heater 21 and sample holder 22 which is interconnected with the heater 21 and located on the lower side thereof. The heater 21 and holder 22 may be withdrawn from or inserted into the upper open end 20 of the housing 18. An insulating material 23 is provided in the casing 12 to surround the outer housing 15. The insulating material 23 may be rock wool or any other suitable material or combination of insulating materials.

Provided at the lower end of the housing 15 is a secondary heating element 24 which is wound around the housing 15. The primary gas heater 21 includes an elongated hollow housing 25 which can be inserted into and received substantially coaxially within the tubular member 18. The housing 25 also has an annular flange or collar 26 which can seat on the projecting upper end 18' of the member 18 and be sealed thereto by an O-ring seal 27 provided on or in an internal annular recess in the flange 26. When the annular flange or collar 26 is in position over the upper end of the housing as shown in FIG. 3, the seal 27 seals the collar 26 to the outer surface of the tubular member 18. The primary heater 21 includes a series of coaxially arranged tubular members 28 and a heating wire or element 29 wound around the tubular members 28. The top of the housing 25 is provided with a connector 30 for connection to a compressed gas or air source such as a compressor via a suitable control valve. The housing 25 also carries terminals 31 for connecting the heater wire or element 29 to a source of power.

In use when compressed gas such as compressed air is supplied from the compressed air or gas source to the inlet connector 30 and current is supplied to the heating element 29, air passes as indicated by the arrows in FIG. 3 in a serpentine manner between the tubes 28 and past the heating element 29 to exit at 32 at the lower end of the heating unit 21.

The housing 25 suitably at the collar 26 also includes diametrically arranged connectors 33 which can connect to the flange 19 so that housing 25 and tubular member 18 can be interconnected for a purpose described further below The connectors 33 each include a threaded rod 34 having a head or nut 35 at one end and the flange 19 (or a bracket attached to the flange 19) has a slot which can receive the rod 34 therethrough and act as a stop to the with the head 35. The respective threaded rods 34 are also threadedly engaged with internally threaded lug 37 arranged on diametrically opposite sides on the collar 36 and hand actuated lock nuts 38 are engaged with the rod 35.

Figure 5:
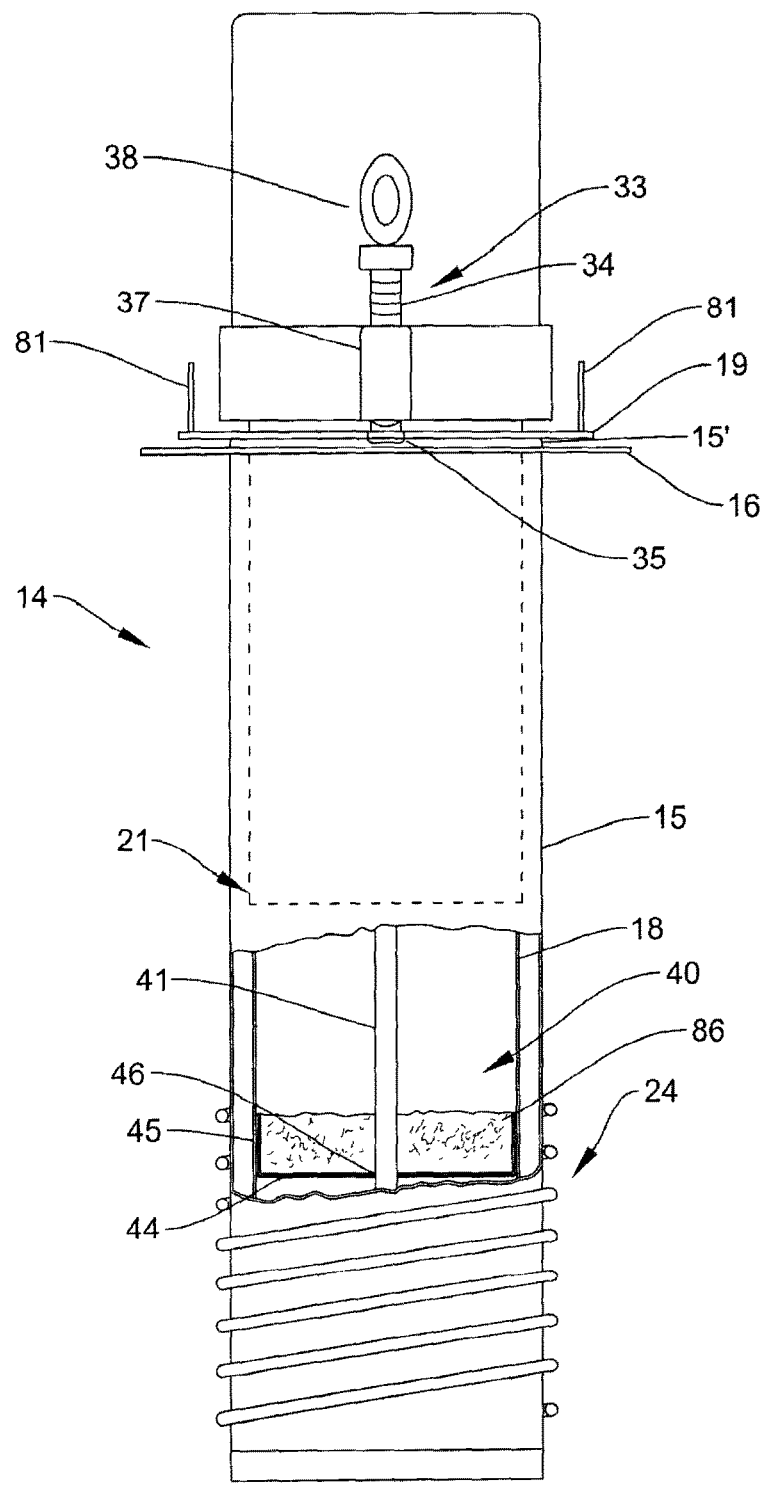
FIG. 5 is a partly cut away view of the soil sample holder and heating chamber for heating soil samples.

The soil sample holder 22 includes a series of soil sample holding units 40 which are arranged in use in spaced apart positions along a central shaft 41 which is secured at its upper end to the heating unit 21. Each soil sample holding unit 40 is of the same configuration as that disclosed in FIGS. 14 and 15 of my aforesaid International patent application PCT/AU2013/001511 including as shown in FIGS. 3 and 5, a rigid holder 43 comprising an air or gas permeable grid or mesh member 44 of a diameter similar to the internal diameter of the tubular member 18. The holders 42 may be fixed to the shaft 41 or may be adjustable along the shaft 41 and fixed at various positions along the shaft 41.

To prevent or minimize escape of fine soil particles, the soil sample holding unit 40 may be used with a flexible cup shaped member 45 formed of a fabric or other pliable material which is air or gas permeable which can seat on the grid or mesh member 44. The fabric or other pliable material preferably comprises an air or gas permeable material which can handle the temperatures encountered in the apparatus 10. A suitable material may comprise a woven fibreglass cloth. The gas permeable member 45 may be formed or shaped from material which is initially in a flat form which can be folded into a generally cup-shaped configuration. The cup shaped member 45 is also provided with a central opening 46 which can neatly but firmly receive the shaft 41 and substantially seal thereagainst.

The lower end of the housing 15 extends through the base 47 of the outer casing 12 as at 48 and a collection device 49 which comprises a tray 50 can be moved to a position directly below the extended lower end of the housing 15 as shown in FIG. 3. This enables any particles of soil or other materials in samples held on the sample holder 40 which is forced through or past the grid 44 and permeable fabric 45 supported on the grid 44 collect on the tray 50. These materials can then be weighed and adjustments then can be made to the initial weight of the soil samples as described below.

The collection tray 50 is located within a chamber 51 which is defined by one leg 52 of an exhaust duct 53 which is located and suspended in an horizontal attitude beneath the casing 12. The leg 52 of the duct 53 is connected at the rear of the casing 12 to, and communicates with, an upright leg 54 of the duct 53 which is open at its upper end 55 and which serves as a chimney or vent to direct hot gases upwardly away from the casing 11.

As shown also in FIGS. 1 and 2, the leg 52 of the duct 53 extends forwardly to terminate at a position 56 in substantial alignment with the front wall of the casing 11. A bracket 57 which is an upwardly bent portion of the top flange of the duct leg 52 secures the leg 52 by the use of mechanical fasteners such as rivets to the front of the casing 11. The collection tray 50 is of slightly less width than the internal width of the duct leg 52 and includes a planar base 58 which seats on the lower flange of the duct leg 52 so as to be supported for sliding movement thereon. The tray 50 additionally includes opposite upright side flanges 59 which serve to constrain materials deposit onto the tray 50. Furthermore the tray 50 at its outer end is provided with an upright face member 60 so that the collection tray 50 is in somewhat of a drawer configuration. The face member 60 is peripherally larger than the cross section of the duct leg 52 such that when in the FIG. 3 position, the face member 60 overlies the opening 61 into the duct leg 53 to substantially close the opening 61 whilst in the FIG. 1 and dotted outline position of FIG. 2, the collection tray 50 is slid outwardly of the duct leg 52 so that the face member 60 is moved clear of the opening 61 to open the outer end of the leg 52 to the external atmosphere.

The apparatus 10 also includes an upstanding mast 62 which extends parallel to the duct leg 54 and which is mounted at its lower end on an upright spigot 63 on the top wall 17 of casing 11 for rotation about its longitudinal axis. Brackets 64 support the mast 62 to the duct leg 54 and allow for this rotational motion. A handle 65 fixed to the lower end of the mast 62 can be grasped to enable the mast 62 to be pivoted by hand in opposite directions. At its upper end the mast 62 has an outwardly extending arm 66 which carries a winch 67 at its free end, the cable 68 of the winch 67 being connected to a lifting eye 69 on the housing 25 so that the primary heating unit 21 and soil sample holder 22 (and tubular housing 18) can be raised or lowered. In addition, the mast 62 is provided with a radially outwardly extending support arm 70 which when rotated with or relative to the mast 62 can be moved to a position beneath respective sample holding units 40 so as to support the primary heating unit 21 and sample holder 22 whilst each holding unit 40 is being loaded with a soil sample.

For additional cooling of the apparatus 10 after its use and for rapid turnaround, a pipe 71 is provided for introducing a flow of air into the upright duct leg 54 as shown in FIGS. 2 and 3. The pipe 71 is in the form of an elbow having a first upright portion 72 and a second horizontal portion 73 which penetrates the wall of the duct leg 54 and which is connected to an air blower 74. Alternately the portion 73 of the elbow 71 may be connected to a remote source of air such as a compressor.

For obtaining an indication of the changes of weight of the soil samples consequent of heating thereof, the apparatus 10 may incorporate a balance scale including a balance beam 75 (show in dotted outline in FIG. 1, and in FIG. 6) which has opposite parallel arms 76 which are supported at a knife-edge fulcrum 77 intermediate their ends defined by blades 78 supported on brackets 79 extending from one side of the casing 11. For support of the heater 21 and soil sample holder 22, brackets 80 on the annular flange 18 incorporate spaced apart hangers 81 for suspending the housing 18 and attached heater 21 and holder 22 in the manner described further below.

A variable counter- or balance weight 82 is supported to the arms 76 on the opposite side of the fulcrum 77 by means of a hanger/knife edge connection 83 similar to that for the housing 18. The housing 18 and balance weight 82 are arranged at equispaced positions on opposite sides of the fulcrum 77 of the beam 73. The counter weight 82 may include a beaker or container 84 to which a liquid such as water can be added or removed to balance the beam 73. The counter or balance weight 82 can also include or comprise fixed or variable weights 85 (see FIG. 3).

In use samples of soil 86 taken from an area where carbon content is to be assessed is screened to remove all fibrous material such as plant and animal material not yet decomposed and the soil samples are then placed within the respective holders 43 by operating the winch 67 to elevate the heater 21 and soil sample holder 22, then lowering and filling each unit 40 in turn during which they are supported by the support arm 66 which can be pivoted between a non-supporting position and a supporting position. After the soil sample holder 22 has been inserted endwise into the upper end of the housing 18 the heater 21 follows being lowered so that it the housing 25 seals through the seal 26 to the upper end of the housing 18. The collar 26 of the housing 25 may then be secured to the flange 19 by the threaded rod connectors 34.

Figure 6:
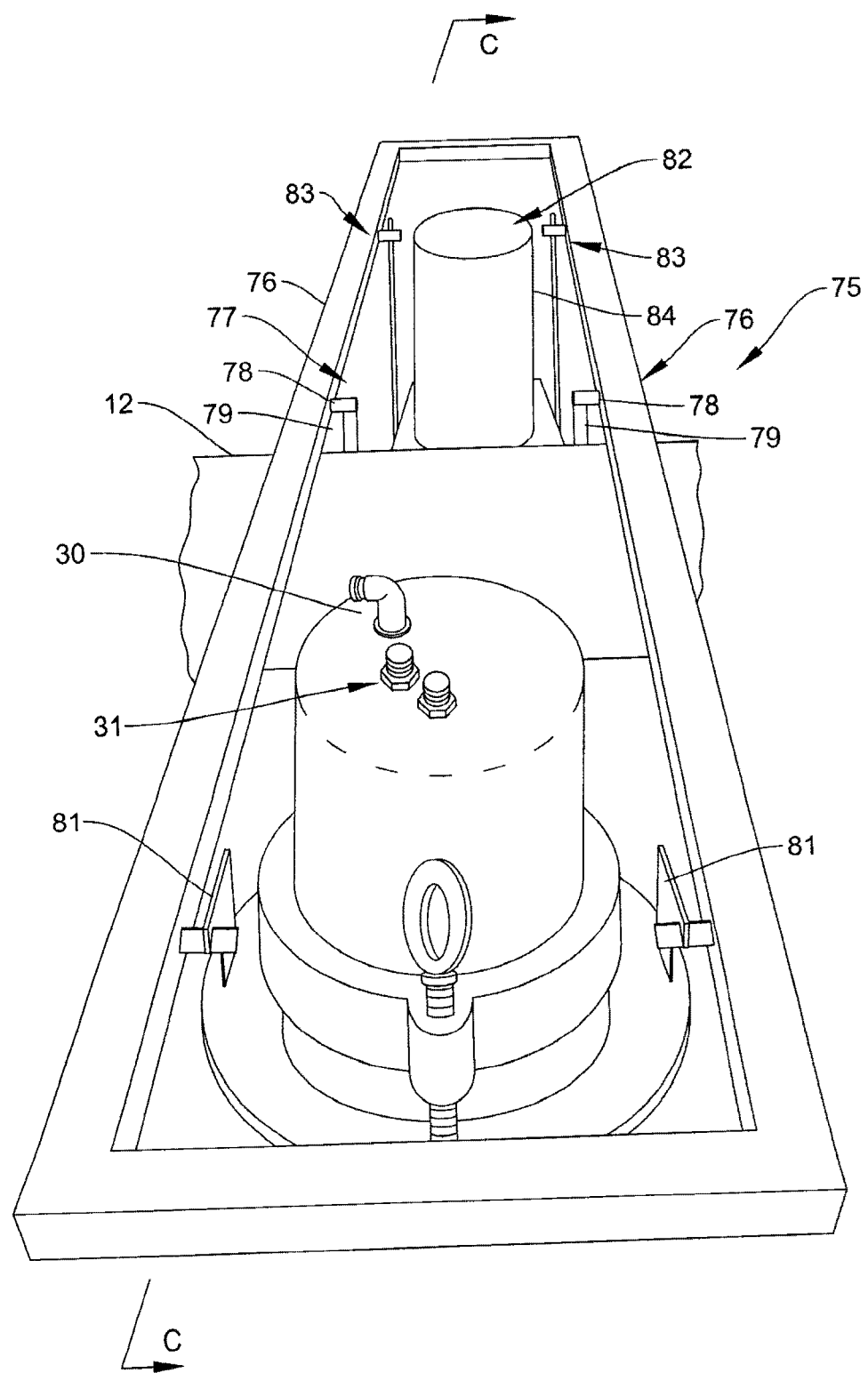
FIG. 6 illustrates weighing apparatus for weighing the soil samples in situ.
Figure 9:
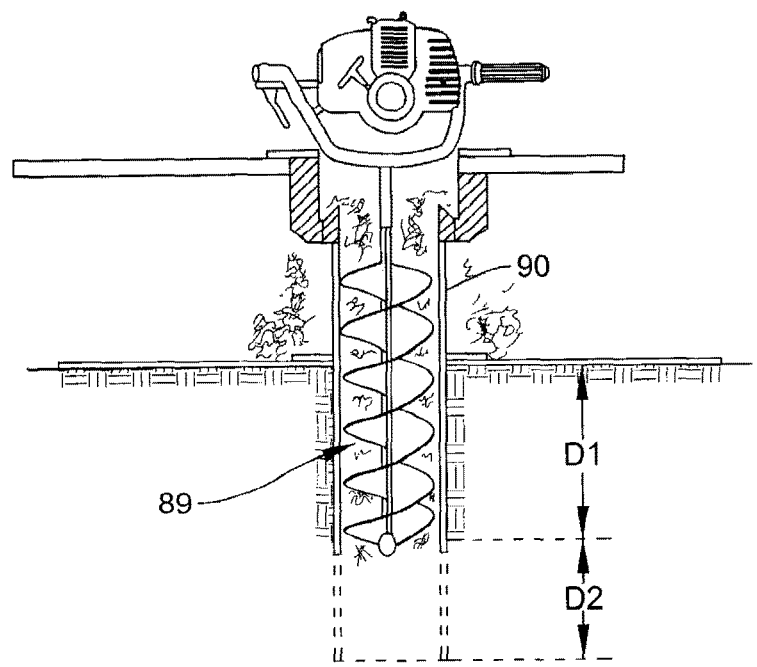
FIG. 9 illustrates an auger for obtaining soil samples.

For heating of the soil samples, the housing 25 and attached housing 15 are suspended on the beam 75 are initially urged downwardly into the outer housing 18 until the flange 19 seats on the upper end 15' of the housing 15 as shown in FIGS. 6 and 7. In this position as shown in FIG. 3, the beam 75 will not be in balance and a weight may be applied to the housing end 25 of the beam 75 to maintain the unit in the position of FIGS. 2 and 3. In this position, the annular space 87 between the housings 15 and 18 will be closed or sealed at its upper end to prevent upward flow of air in this space. Current can then be applied to the heater element 29 and compressed air or gas supplied from the compressed air or gas *source via the connector 30. Air will be forced through the heater 14 past the element 29 to be heated and exit at the lower end 43 of the heater 21 and the heated air will then be forced through the soil samples 86. Initially the heating unit 14 is operated to remove moisture from the soil samples 86 to dry the soil sample/s 86. When the sensed temperature increases above 100° C. which is the boiling point of water or moisture within the soil samples 86, the soil samples 86 will be dry. The weight holding the apparatus 10 in the position of FIGS. 1 and 2 is removed and weight may be applied to the counter weight 83 for example by adding liquid to the beaker 85 until the beam 77 is balanced for example as shown in FIG. 7. This provides an indication of the weight of the soil samples 86 after the drying process and prior to the carbon removal process.

The beam 75 is then returned to the position of FIG. 6 in which the flange 19 of housing 18 seats on the upper end of the housing 15 and current applied to the heating element 29 and compressed gas supplied through the connection 30. Typically the samples 86 are heated to temperatures above or in the region of 375° C. and maintained at those temperatures for an extended period of time for example 10-60 minutes to ensure that organic carbon and other organic materials are burnt off. This temperature and time however can be varied by varying current supply to the heater 21 and also by varying the air or gas supply. To ensure that the temperature of the soil samples does not increase beyond predetermined limits, gas flow through the samples may be restricted. This restricts the volume of oxygen supply to thereby prevent excessive burning of materials within the soil samples. The heating time and temperature of air or gas supplied may also be varied depending up the samples being tested. The balance beam 75 may then be released and balanced by adding liquid to the container. The weight of the added liquid corrected by taking into account losses due to the weight of materials collecting on the tray 49 will correlate to the organic carbon content in the soil samples.

To enable the test results to be validated, it is preferred for efficiency of operation that the apparatus 10 be cooled and for that purpose, the collection tray 49 is slid outwardly to the position of FIGS. 1 and 2 which opens the opening 61 to the duct leg 52 to the external atmosphere. Compressed air is continued to be supplied through inlet 39 to flow through the housing 15 to cool the apparatus 10, that air flowing downwardly into the legs 52 and 54 of the duct 53 whilst flow of air outwardly through upper end 55 of the duct leg 54 induces a back pressure in the duct leg 52 and causing air to be drawn from externally of the casing 11 into the opening 54. This will result in enhanced cooling of the apparatus.

Figure 4:
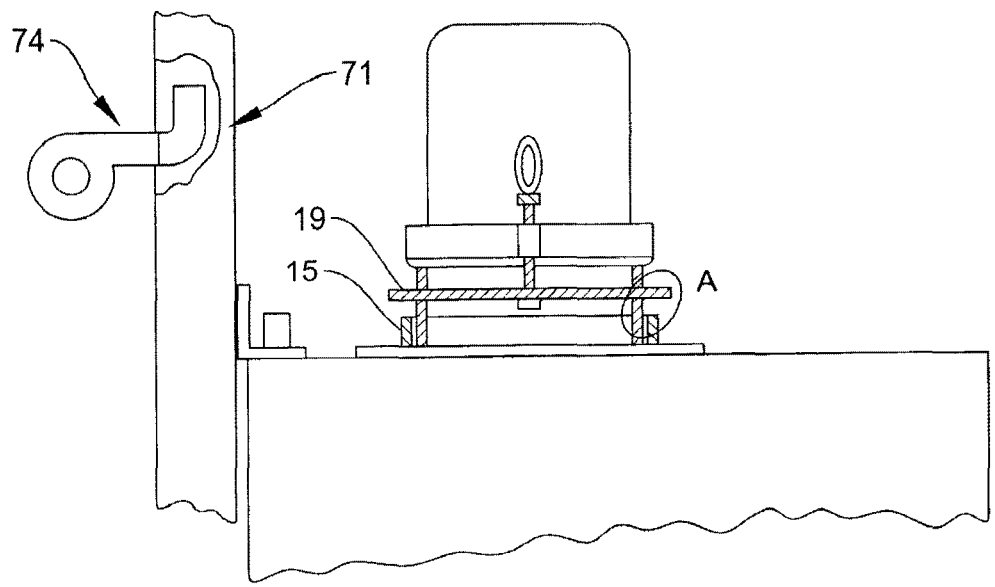
FIG. 4 is a side view of part of the apparatus when undergoing cooling.
Figure 4A:
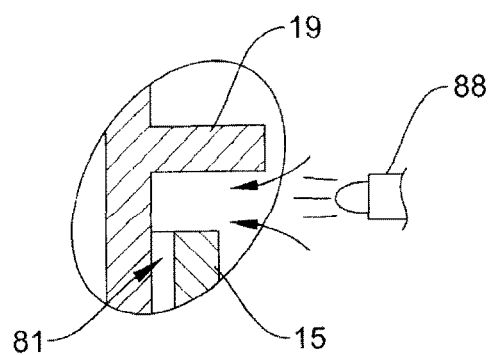
FIG. 4A is a sectional enlarged view of the region A of FIG. 4.

For additional or alternate cooling of the apparatus 10, the blower 74 is operated to inject a flow of air through the elbow 71 into the duct leg 54 with air flowing upwardly as indicated by the arrows in FIG. 4. At the same time or prior to operation of the blower 74, the winch 67 is operated to raise the air heater 21, connected sample hold 22 and inner tubular member 18 which is connected to the housing 25 through the threaded connectors 34. This also causes the flange 19 which is provided adjacent to the upper end of the tubular member 18 to be raised above the upper edge 15' of the tubular housing 15 as shown in FIGS. 4 and 4A. This opens the annular space 87 between the tubular members 15 and 18 to the external atmosphere. Air supplied to the duct leg 54 creates a back pressure in the duct leg 52 and causing air to be drawn from externally of the apparatus 10 into the annular space 87 and downwardly through that space which will result in rapid cooling of the apparatus 10. The collection tray 49 may also be slid open or partly open to the position shown in FIG. 1 and in dotted outline in FIG. 2 so that external air is drawn into the chamber 51 for further cooling of the apparatus 10. Additional cooling can be achieved by the use of a water source such as a water spray nozzle 88 as shown in FIG. 4B. The spray nozzle 88 may be operated when the blower or fan 71 is operating and when the inner housing 18 is elevated as in FIGS. 4 and 4A so that water is drawn into the annular space 87 within the tubular member 15.

To validate the results of the above test, a sample of soil, say around one and a half kilograms, is extracted from an area immediately adjacent to, and having the same geological structure as, the region from where the soil sample being tested has been obtained. That sample is heated to remove all organic materials including organic carbon such as by the method and using the apparatus describe above (or by other means). The sample subsequent to its heating to remove organic materials can thus be weighed and used as an "inert base".

The soil samples may be extracted by using as shown in FIG. 12 a powered auger 89 operating in a tube 90 as for example of the type disclosed in my International Patent Application PCT/AU2017/050648. The auger 89 may be inserted into the ground and operated to a depth D1 so that all the soil within that depth is removed to provide the first sample for testing for organic carbon content. Continued operation of the auger 89 downwards to the additional depth D2 into the subsoil will provide a second sample for use in validating the test performed on the first sample. The second subsoil sample can be expected to contain negligible soil organic matter thus can be used as the zero organic matter content point from which both increases and levels of organic matter content can be determined.

If it is suspected that this sample from the D2 depth contains organic materials, a sub-sample from of this material can be heated in the apparatus described above to burn off any suspected organic materials so that it can be used as a truly organic matter free and inert base. It is noted that any material that is not organic matter, such as structural water can also be removed in this heating process.

Sub samples derived from either of the above methods are weighed after drying heating and removal from the oven 12 and to those base sub-samples can be added some carefully weighed sample of (usually unavoidably moist) organic matter, typically peat. The samples of soil containing the added organic matter are subject to an additional re-drying and re-weighing from which the dry weight of the added organic matter or peat is determined then a Loss on Ignition (LOI) test, such as tests using the apparatus described above, and the loss in weight measured. If the loss in weight equals the weight of the added organic matter, the test of the first sample will be validated with the calculated carbon content thereof being correct.

If the test using the base which has been subject the LOI shows a greater LOI loss than predicted then a chemical reaction must have happened between (probably) the carbon in the organic matter and the already "cooked", and therefore, supposedly, inert sample material. This could, for example, show the presence of a hematite to magnetite reaction. Thus an adjustment of the results of the test on the first sample will need to be made to obtain the correct organic carbon content of the sample. This adjustment may be made on a pro-rata basis If the LOI testing of the base which has not been subject to a LOI test before the peat has been added is then subject to a LOI test, that test will show a LOI weight loss which can be considered to be the same as would result from a test of on a nearby soil which has a weight of organic matter content exactly the same as the weight of peat added to the subsoil material.

Figure 10:
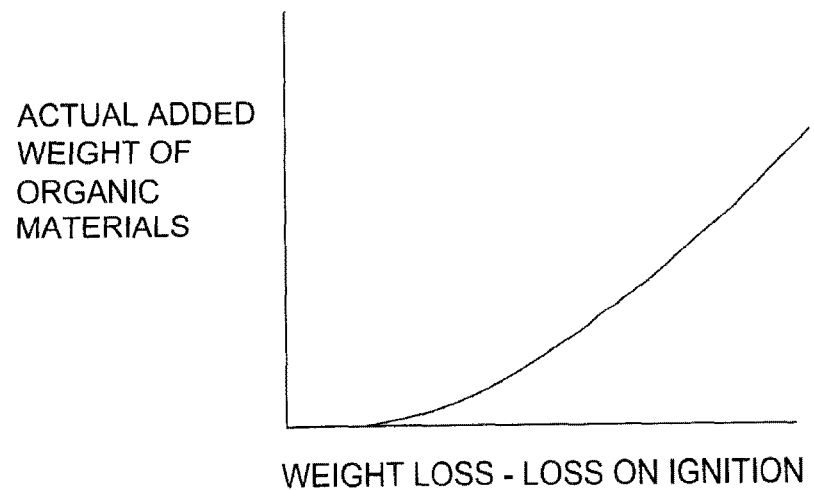
FIG. 10 is a graph showing loss in ignition plotted against added amount of organic material in the test validation procedures.

If different an adjustment may be made on a pro-rata basis however for more accurate results, a series of Loss on Ignition (LOI) tests can be carried out using the subsoil material which contains no organic matter or little organic matter to which is added a different but known quantity of organic matter. By taking a series of tests a graph, as shown in FIG. 10 can then be drawn which plots the tested by Loss on Ignition (LOI) weights against the known weight of organic matter added to each sample. This graph can be used to show that when any future sample, taken from the same general location is subjected to a Loss On Ignition test the Loss on Ignition weight thus determined can be applied to the graph and the true organic matter content of the soil can be seen and carbon content determined.

The validation procedures described above avoids the possible issue of an "organic matter chemical combination with the soil material" problem as can occur with the conversion of hematite to magnetite.

With most soil types, the quantity of organic matter determined can be used to accurately estimate the actual total weight of organic carbon in any nominated area of land and thus assist in estimating a national as is required in the Kyoto Protocol. However, determining the total weight is only of such academic interest as the prime concern is ending global warming, and therefore it is measuring specific increases in soil carbon and then being able to reward farmers for those increases.

It will be appreciated that the apparatus of the invention may be in many different configurations other than that illustrated and described to perform the method of the invention. Whilst the method has been described where soil samples are heated by forcing hot air through the samples to dry the samples and/or remove carbon from the samples, the validation method of the invention may equally be applied to other Loss on Ignition (LOI) techniques used for determining the organic carbon content of a soil sample. Many different arrangements may also be used for the weighing of the soil sample or samples or apparatus or housing which contains the soil sample or samples other than the arrangement described in the embodiment.

Any reference to prior art herein is not to be taken as an acknowledgement that such art constitutes common general knowledge. Further, the terms "comprising" or "comprises" as used throughout the specification and claims are taken to specify the presence of the stated features, integers and components referred to but not preclude the presence or addition of one or more other feature/s, integer/s, component/s or group thereof.

The invention claimed is:

1. A method of validating a test for estimating the organic carbon content of soil or changes in organic carbon content of said soil over time in which a first sample of said soil is taken from a selected location and heated using Loss On Ignition (LOI) to remove organic materials including organic carbon from said soil sample by burning off or oxidising said organic materials, said method comprising the steps of taking at least one further sample of soil from a location immediately adjacent to, and having the same geological structure as said selected location, said sample having or being treated to have minimal organic material content, adding to said further sample, a predetermined quantity of an organic material to provide a second sample, heating said second sample containing said quantity of organic material using Loss On Ignition (LOI) to burn off said quantity of organic material, and monitoring the change of weight of said second sample due to the burning off of said organic materials.

2. A method as claimed in claim 1 wherein if the monitored change of weight of said second sample is equal to the weight of added said organic material, the test on said first sample will be valid.

3. A method as claimed in claim 1 wherein if the monitored change of weight of said the second sample differs from the weight of added said organic material, the test on said first sample will be invalid.

4. A method as claimed in claim 1 wherein a plurality of further samples are obtained from said location immediately adjacent said selected location and wherein different quantities of said organic materials are added to said further samples, said further samples being heated to burn off organic materials using Loss On Ignition (LOI) and wherein the change of weight of said further samples is indicative of the weight of said added organic materials.

5. A method as claimed in claim 1 wherein said at least one further sample is treated by using a Loss On Ignition procedure to remove by burning off organic materials in said sample prior to addition of said predetermined quantity of said organic material.

6. A method as claimed in claim 5 wherein said samples are obtained using an auger, said auger being operated to a first depth at said selected location to extract materials to provide said sample.

7. A method as claimed in claim 6 wherein continued operation of said auger to depths below said first depth provides materials for said further sample.

8. A method as claimed in claim 1 wherein said organic material added to the soil sample comprises peat.

9. A method as claimed in claim 1 wherein each soil sample in turn is supported on one or more gas permeable means, and wherein heated gas is forced through said soil sample, the change of weight of said soil sample correlating to the organic carbon content of the soil sample.

10. A method as claim 9 wherein soil particles forced through or past said gas permeable means are collected, and wherein the change of weight of the soil samples adjusted for the weight of said collected soil particles is an indication of the organic carbon content in the soil sample.

11. Apparatus for obtaining an indication or assessment of the carbon content of soil and/or variations of the carbon content in soil in accordance with the method of claim 10, said apparatus comprising an upright housing defining a chamber, a soil sample holder for supporting one or more samples of said soil within said chamber, means for forcing heated gas through said chamber and the soil sample or samples therein to remove organic materials including carbon from the soil, means for collecting the soil particles forced through or past said soil sample holder and means for measuring the change of weight of said soil sample or samples adjusted for the weight of said collected soil particles to provide an indication or assessment of carbon content in the soil.

12. Apparatus as claimed in claim 11 wherein said housing is received coaxially within an outer tubular housing such that the walls of the respective housings are juxtaposed, said outer tubular housing being arranged within an outer casing and is surrounded by an insulating material.

13. Apparatus as claimed in claim 12 wherein said upright housing is provided with an annular flange adapted to seat upon an upper end of said outer tubular housing, said outer tubular housing being movable longitudinally of said outer housing to lift said annular flange above said upper end of said outer tubular housing to open the space between said housings to the external atmosphere for cooling of said apparatus.

14. Apparatus as claimed in claim 13 and including means for spraying coolant towards the upper end of said outer housing for entry into the space between said inner and outer housings.

15. Apparatus as claimed in claim 11 wherein said particle collection device is located within a chamber vertically beneath the housings and wherein the outer housing or an extended portion thereof extends into the chamber.

16. Apparatus as claimed in claim 15 wherein said particle collection device is in the form of a tray which is slidably movable within the chamber.

17. Apparatus as claimed in claim 16 wherein said chamber is defined by a horizontally extending duct and wherein the lower portion of the outer housing extends into the duct.

18. Apparatus as claimed in claim 17 wherein said horizontally extending duct is joined at one end to a vertically extending duct which acts as a stack or chimney for discharge of hot air of gases from the apparatus.

19. Apparatus as claimed in claim 18 wherein the opposite end of the horizontally extending duct is open and wherein the collection device includes a face member wherein when the collection device is slid in a first direction the facing member can overly and close the duct opening and wherein whorl the collection device is slid in an opposite direction, said facing member moves away from and opens the opening.

20. Apparatus as claimed in claim 19 wherein when the opening is open, air forced into the apparatus cools the apparatus and when flowing through the stack, or chimney creates a back pressure which will induce a further flow or air into the apparatus through the opened duct.

* * * * *